United States Patent
Krufka et al.

(10) Patent No.: US 7,150,190 B2
(45) Date of Patent: Dec. 19, 2006

(54) METHOD AND APPARATUS FOR CAPACITIVELY DETERMINING THE UPPERMOST LEVEL OF A LIQUID IN A CONTAINER

(75) Inventors: Frank S. Krufka, Kirkwood, PA (US); Joson Kunnumpuram Joseph, Bear, DE (US); Arnold Lloyd Lewis, Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 109 days.

(21) Appl. No.: 11/085,660

(22) Filed: Mar. 21, 2005

(65) Prior Publication Data

US 2006/0207322 A1    Sep. 21, 2006

(51) Int. Cl.
*G01F 23/26* (2006.01)
(52) U.S. Cl. ............... 73/304 C; 73/290 R; 73/864.01
(58) Field of Classification Search .......... 73/304 R, 73/290 R, 864.01
See application file for complete search history.

(56) References Cited

U.S. PATENT DOCUMENTS

| | | | | |
|---|---|---|---|---|
| 3,720,211 A | * | 3/1973 | Kyrias | 604/155 |
| 3,807,231 A | * | 4/1974 | Spaw | 73/290 R |
| 4,078,895 A | * | 3/1978 | Moran | 422/66 |
| 4,326,851 A | * | 4/1982 | Bello et al. | 73/304 C |
| 4,485,673 A | * | 12/1984 | Stern | 73/304 C |
| 4,851,831 A | * | 7/1989 | Stern | 340/870.16 |
| 4,908,783 A | | 3/1990 | Maier | 702/52 |
| 5,049,878 A | * | 9/1991 | Stern | 340/870.4 |
| 5,051,921 A | | 9/1991 | Paglione | 702/52 |
| 5,083,470 A | | 1/1992 | Davis et al. | 73/864.24 |
| 5,104,621 A | * | 4/1992 | Pfost et al. | 422/67 |
| 5,108,703 A | * | 4/1992 | Pfost et al. | 422/65 |
| 5,125,748 A | * | 6/1992 | Bjornson et al. | 356/414 |
| 5,139,744 A | * | 8/1992 | Kowalski | 422/67 |
| 5,206,568 A | * | 4/1993 | Bjornson et al. | 318/568.1 |
| 5,212,992 A | * | 5/1993 | Calhoun et al. | 73/864.01 |
| 5,365,783 A | | 11/1994 | Zweifel | 73/304 C |
| 5,369,566 A | * | 11/1994 | Pfost et al. | 700/18 |
| 5,437,184 A | | 8/1995 | Shillady | 73/304 C |
| 5,451,940 A | | 9/1995 | Schneider et al. | 340/870.37 |
| 5,493,922 A | | 2/1996 | Ramey et al. | 73/863.02 |
| 5,582,798 A | * | 12/1996 | Meltzer | 422/100 |
| 5,600,997 A | | 2/1997 | Kemp et al. | 73/290 V |
| 6,101,873 A | | 8/2000 | Kawakatsu et al. | 73/304 C |
| 6,643,132 B1 | | 11/2003 | Faneuf et al. | 361/700 |

* cited by examiner

*Primary Examiner*—Helen Kwok
*Assistant Examiner*—Rodney Frank
(74) *Attorney, Agent, or Firm*—Leland K. Jordan

(57) ABSTRACT

A liquid level sensor confirms actual physical contact between a probe and a liquid by verifying that any change in capacitance of the sensor is constant over a given time period and thereby is not caused by spurious electrical disturbances or other measuring irregularities.

8 Claims, 5 Drawing Sheets

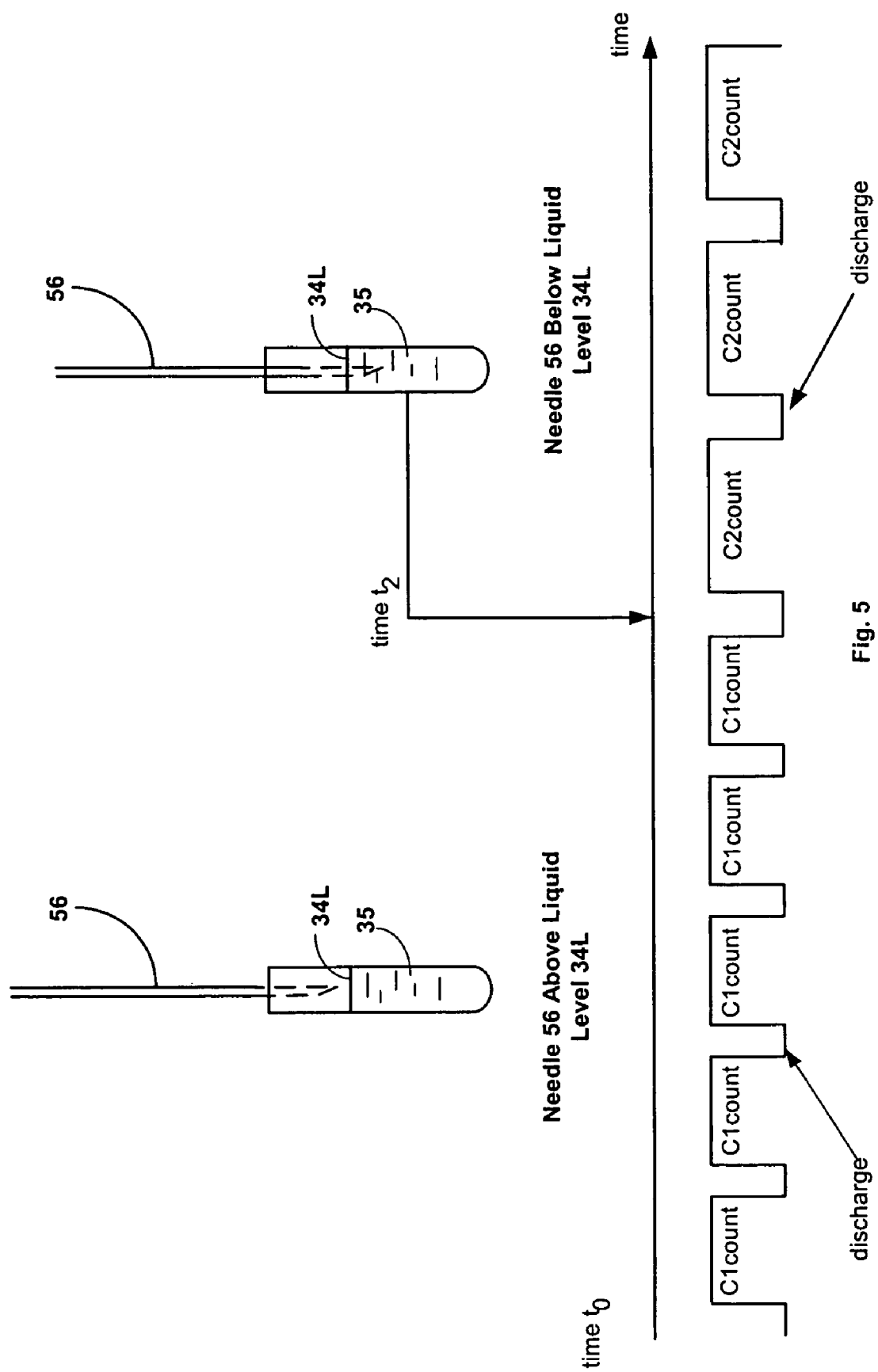

METHOD AND APPARATUS FOR CAPACITIVELY DETERMINING THE UPPERMOST LEVEL OF A LIQUID IN A CONTAINER

FIELD OF THE INVENTION

The present invention relates to a method and apparatus for aspirating liquid samples, reagents, or other solutions from a container using a probe. In particular, the present invention provides a method for determining the uppermost level of liquid within the container so that a precisely predetermined volume of liquid may be aspirated from the container into the probe.

BACKGROUND OF THE INVENTION

Various types of analytical tests related to patient diagnosis and therapy can be performed by analysis of a liquid sample taken from a patient's infections, bodily fluids or abscesses. These assays are typically conducted with automated clinical analyzers onto which tubes or vials containing patient samples have been loaded. The analyzer extracts a pre-determined volume of liquid sample, typically in the range of 1–3 mL, from the vial using an appropriate probe and combines the sample with various reagents in special reaction cuvettes. Analytical measurements are often performed using a beam of interrogating radiation interacting with the sample-reagent combination, for example turbidimetric, fluorometric, absorption readings or the like. The measurements allow determination of end-point or reaction rate values from which an amount of analyte related to the health of the patient may be determined.

An important aspect of maintaining analytical accuracy in such analyzers is the ability to precisely extract the pre-determined volume of liquid sample from the vial. At the same time, in order to minimize cross contamination between samples and reagents and facilitating cleaning the tip the probe, it is desired to minimize contact between the probe and the liquid. Therefore the probe is introduced into the liquid container and preferably maintained a short distance below the surface of the liquid. Liquid aspiration is then accomplished by either aspirating the pre-determined volume while the probe is stationary (for very small volumes) or moving the probe further into the probe during aspiration (for larger volumes).

Various methods have been implemented to locate the uppermost level of liquid in the container, frequently employing capacitive level sensors. Such sensors are based on the fact that any charged conductor, like a probe in air, exhibits a finite electrical capacitance relative to a ground and this capacitance will change if the probe is placed in contact with a medium other than air. In particular, when the probe contacts liquid, its dielectric constant increases above that in air and the greater surface area of the liquid results in an increased probe capacitance. These capacitance changes can be very small so that sensitive detection devices are required and these must be free of false signals arising from electrical disturbances, contaminations, bubbles and the like.

U.S. Pat. No. 6,164,132 discloses a capacitive liquid level sensor having a capacitive sensor array superposed on each side of a dielectric substrate, wherein the sensor signal detection electronics are located immediately adjacent each capacitive sensor. These provisions result in high sensitivity of detection of submergence in the liquid, as well as essentially eliminating parasitic electric fields. The preferred capacitive sensors are interdigitated capacitors, and the preferred sensor signal detection circuit is an RC bridge and a comparator. The sensitivity of the capacitive liquid level sensor allows a reference capacitive sensor to be obviated, so that there are no false indications of liquid level due to any film of the liquid clinging to an exposed portion of the capacitive liquid level sensor.

U.S. Pat. No. 5,493,922 discloses a liquid level sensor control circuit for controlling the position of a sampling probe relative to a liquid in a container. The apparatus includes a sampling probe, an oscillator circuit coupled to the sampling probe for producing a first output signal having a constant frequency, a comparator coupled to the oscillator circuit for comparing the amplitude of the first output signal to a first reference amplitude and for producing a change signal when the amplitude of the first output signal changes with respect to the reference amplitude, and a controller responsive to the change signal for controlling the position of the sampling probe with respect to the surface of the liquid.

U.S. Pat. No. 5,437,184 discloses a capacitive liquid level sensor having phase detecting circuitry in a capacitive sensor array. An X-OR circuit generates a first logic level signal when a difference in the phase of two signals from any two adjacent output plates indicates that a phase difference is present. A second logic signal is generated if no phase difference is detected. The signals are perfectly in phase when any two adjacent output plates are either submerged in fluid or both disposed in air.

U.S. Pat. No. 5,365,783 discloses a computer controlled pipette probe for aspirating or dispensing liquid in the vessel. The charge developed via the capacitance on the probe is coupled to a capacitive sensor circuit which provides a peak detector with an amplified signal representing the peak capacitance between the probe and the liquid. This amplified signal is detected by a peak-capacitance discrimination circuit, the output of which is monitored by the computer for determining the precise position of the probe with respect to the liquid surface level.

U.S. Pat. No. 5,083,470 minimizes false level sensing problems associated with capacitive liquid level sensors by isolating the probe from the connecting tubing by the use of an element exhibiting inductive reactance.

A number of other related U.S. Patents include: U.S. Pat. No. 6,101,873, having a plurality of electrodes positioned vertically from the liquid surface and a level detection circuit for detecting level of the liquid by measuring variations of the capacitance measured between the electrodes; U.S. Pat. No. 5,600,997, wherein a capacitive probe is located at a predetermined desired fluid detection level and when the fluid level recedes, the capacitance of the system changes; U.S. Pat. No. 5,451,940, having a measuring capacitance and at least one reference capacitor; U.S. Pat. No. 5,051,92, using two capacitors to produce a signal proportional to the level of the liquid in the tank and to the composition or dielectric constant of the liquid; and, U.S. Pat. No. 4,908,783, sensing the level of fuel in aircraft fuel tanks using a plurality of capacitive sensors which provide an output capacitance that is a function of the fraction of the sensor wetted by the fuel.

Accordingly, from a study of the different approaches taken in the prior art to provide very sensitive liquid level detection devices, there is a need for an improved approach to ascertain when false signals are generated within capacitive liquid level sensors. In particular, there is a need for a method to confirm that a change in capacitance within a liquid level sensor arise from true physical contact between a probe and a liquid, and that such a change in capacitance is not caused by other factors capable of generating false signals.

SUMMARY OF THE INVENTION

The principal object of the invention is to provide an improved method for confirming that a change in capacitance within a liquid level sensor is caused only by true physical contact between a probe and a liquid. In particular, the present invention verifies that any change in capacitance of the liquid level sensor is repeatable and constant over a given time period and thereby is caused by actual contact the probe and liquid and is not caused by spurious electrical disturbances or other measuring irregularities. This is achieved by repeatedly measuring the amount of time required for the voltage of the system's capacitance to reach a reference value, averaging that amount of charging time over a number of successive readings, identifying any change in the averaged charging time that exceeds a pre-determined value, confirming that such a change in the averaged charging time is stable over a pre-determined time period, and rejecting as invalid any changes in the averaged charging time that are not stable over such pre-determined time period.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
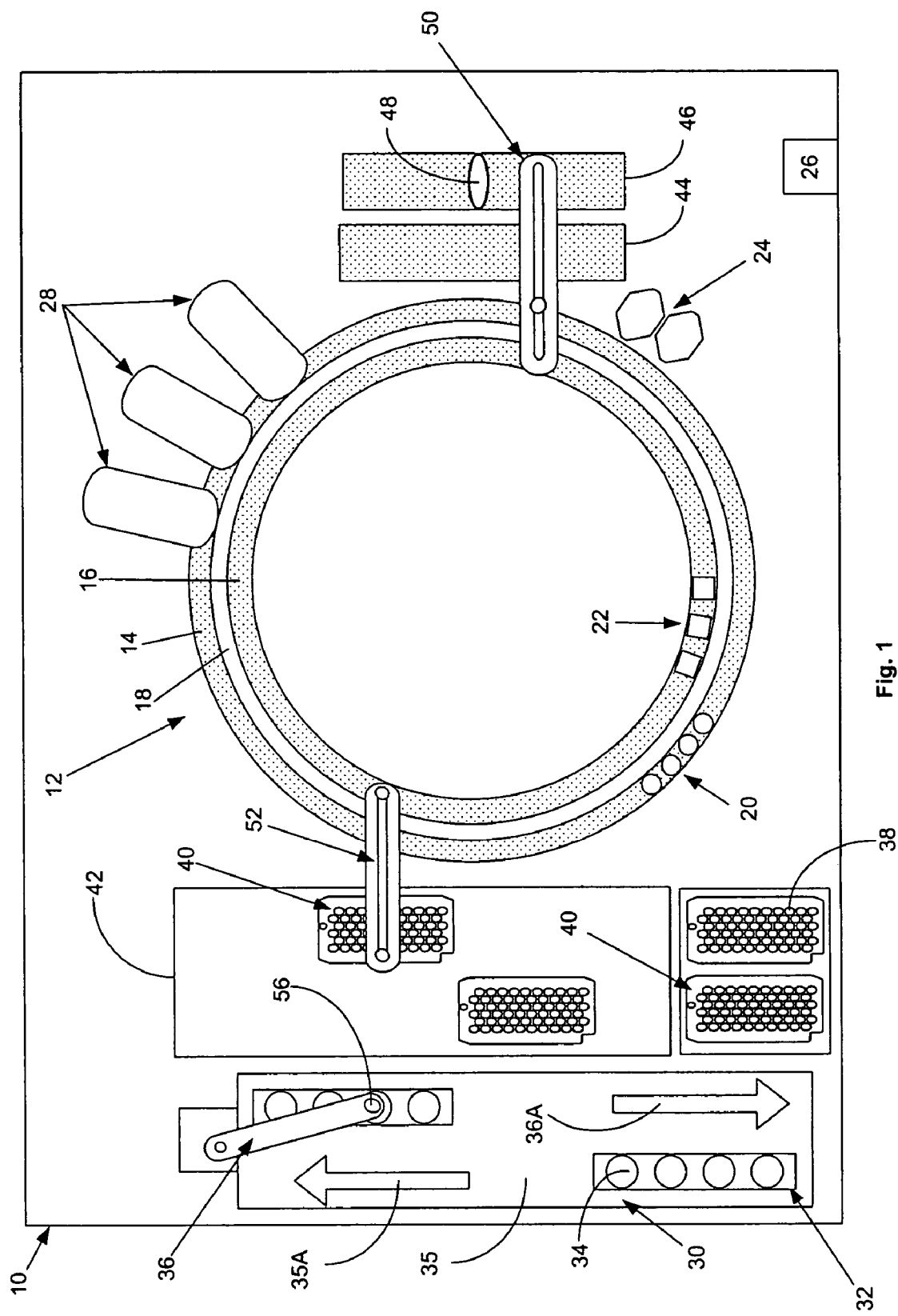
FIG. 1 is a schematic plan view of an automated analyzer in which the present invention may be advantageously employed.

FIG. 1 shows schematically the elements of an automatic chemical analyzer 10 in which the present invention may be advantageously practiced, analyzer 10 comprising a reaction carousel 12 supporting an outer carousel 14 having cuvette ports 20 formed therein and an inner carousel 16 having vessel ports 22 formed therein, the outer carousel 14 and inner carousel 16 being separated by a open groove 18. Cuvette ports 20 are adapted to receive a plurality of reaction cuvettes that contain various reagents and sample liquids for conventional clinical and immunoassay assays while vessel ports 22 are adapted to receive a plurality of reaction vessels that contain specialized reagents for ultra-high sensitivity immunoassays. Reaction carousel 12 is rotatable using step-wise movements in a constant direction, the stepwise movements being separated by a constant dwell time during which reaction carousel 12 is maintained stationary and computer controlled assay operational devices 24, such as measuring devices 28, sensors, reagent add stations, mixing stations and the like, operate as needed on an assay mixture contained within a reaction cuvette or vessel.

Analyzer 10 is controlled by software executed by the computer 26 based on computer programs written in a machine language like that used on the Dimension® clinical chemistry analyzer sold by Dade Behring Inc, of Deerfield, Ill., and widely used by those skilled in the art of computer-based electromechanical control programming.

FIG. 1 shows a bi-directional incoming and outgoing sample fluid tube transport system 30 comprises a mechanism for transporting sample fluid tube racks 32 containing open or closed sample fluid containers such as sample fluid tubes 34 from a rack input load position at a first end of the input lane 35 to the second end of input lane 35 as indicated by open arrow 35A. Liquid specimens contained in sample tubes 34 are identified by reading bar coded indicia placed thereon using a conventional bar code reader to determine, among other items, a patient's identity, tests to be performed, if a sample aliquot is to be retained within analyzer 10 and if so, for what period of time.

A liquid aspiration probe 36 is located proximate the second end of the input lane 35 and is operable to aspirate aliquot portions of sample fluid from sample fluid tubes 34 and to dispense an aliquot portion of the sample fluid into one or more of a plurality of vessels 38 in aliquot vessel array 40, maintained in aliquot vessel array transport system 42, depending on the quantity of sample fluid required to perform the requisite assays and to provide for a sample fluid aliquot to be retained by analyzer 10 within an environmental chamber. After sample fluid is aspirated from all sample fluid tubes 34 on a rack 32 and dispensed into aliquot vessels 38, rack 32 may be moved, as indicated by open arrow 36A, to a front area of analyzer 10 and unloaded from analyzer 10.

Temperature-controlled storage areas or servers 44 and 46 inventory a plurality of multi-compartment elongate reagent cartridges 48 containing reagents accessible by aspiration probes 50 and 52 as necessary to perform clinical assays on sample aliquots removed from sample tubes 34 and dispensed into aliquot vessels 38.

During operation of analyzer 10 using the devices illustrated in FIG. 1, there are several instances when it is critical to aspirate a pre-determined amount of a liquid or liquid solution, for example, from sample tube 34 or reagent container 48, using aspiration probes 36 and 50, respectively. Aspiration may be advantageously accomplished using, for example, the sample aspiration method disclosed in co-pending U.S. patent application Ser. No. 10/871,409. An important aspect of aspirating such liquids is the ability to precisely and accurately ascertain the uppermost level of liquid in said container and a number of methods exist in the art for completing this task. Many of these methods use a capacitive level sensing technique, however, these techniques lack means for verifying that any change in capacitance of the liquid level sensor is caused by actual contact between the probe and a liquid and is not caused by spurious electrical disturbances or other measuring irregularities.

Figure 2:
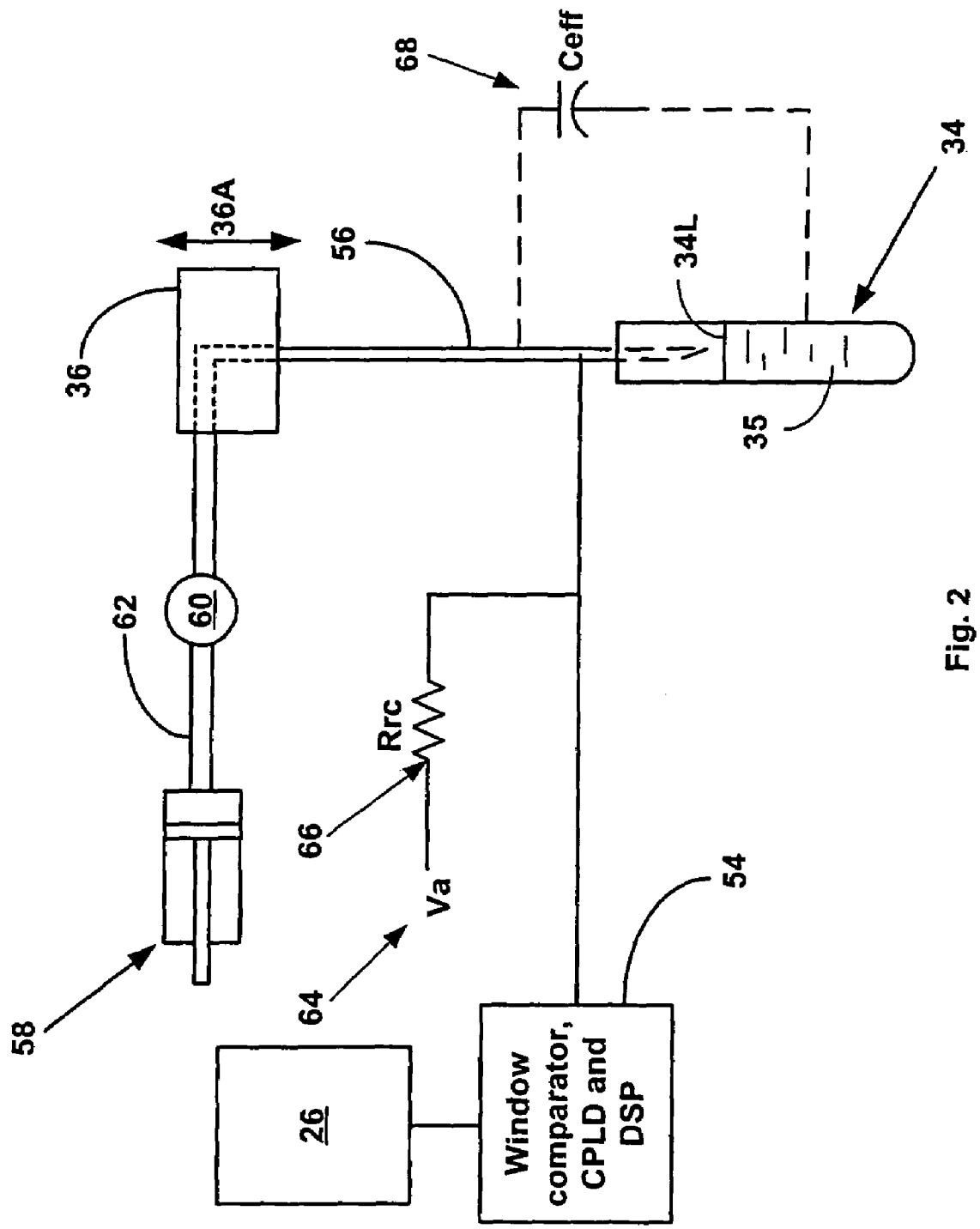
FIG. 2 is a block diagram of the liquid level sensor of the present invention.

The present invention provides means for verifying that a change in capacitance of a liquid level sensor 64 associated with aspiration probes 36, 50 and 52 is not caused by spurious electrical disturbances or other measuring irregularities. FIG. 2 illustrates probe 36 as being vertically moveable over sample tube 34, indicated by arrow 36A, so that a needle portion 56 of probe 36 may be lowered into contact with the uppermost level 34L of a sample liquid 35 contained in tube 34. Aspiration probe 36 is connected to a piston-like pump 58 through a vent valve 60 by means of tubing 62, pump 58 being operable to aspirate and dispense liquid in response to signals from computer 26. A capacitive liquid level sensor 64 is formed by means of an applied voltage Va applied through a known fixed resistor Rrc 66 to needle 56 thereby effectively forming an RC network because of an effective capacitance Ceff 68 formed between needle 56 and liquid 35 within tube 34. An electrical measuring network consisting of a window comparator 54 comprising a pair of operational amplifiers 76, a flip-flop 80, CPLD 82 and DSP 84, described hereinafter, is adapted to compare the voltage in effective capacitance 68 of the RC network to a reference voltage as probe 56 is lowered towards liquid 35, thereby defining capacitive liquid level sensor 64.

As is known, in capacitive liquid level sensors, the voltage in effective capacitance 68 will remain essentially constant because of the air gap between probe 56 and the uppermost level 34L of liquid 35 until probe 56 physically contacts the uppermost level 34L of liquid 35, at which instance the voltage in effective capacitance 68 will increase sharply. The present invention is an improvement over prior art sensors that may be adversely affected by the presence of foam, bubbles or other surface irregularities in that the present capacitive liquid level sensor 64 repeatedly measures the amount of time required for the voltage in effective capacitance 68 to charge to a reference value, averages that amount of charging time over a number of successive readings, and identifies any change in the averaged charging time that exceeds a pre-determined value.

Another problem with known capacitive liquid level measuring systems is dependence upon the sensitivity of the electronic circuitry for monitoring the change in voltage level. If this sensitivity is too low or drifts over time, the sensed voltage level change will be skewed and the system will be unable to accurately compare the change in voltage level to a threshold reference level. An even further problem with such capacitive liquid level measuring systems is that the sensed RC voltage level may not reach the threshold reference level when tube 34 contains very small amounts of liquid. Systems using a fixed threshold level are not useful in such instances, and systems with a variable threshold level require an undesirable calibration process. The present invention avoids problems like these encountered in the prior art by confirming that the previously identified change in the averaged charging time is stable over a pre-determined time period, and rejects as invalid any changes in the averaged charging time that are not stable over the previously identified pre-determined time period.

Figure 3:
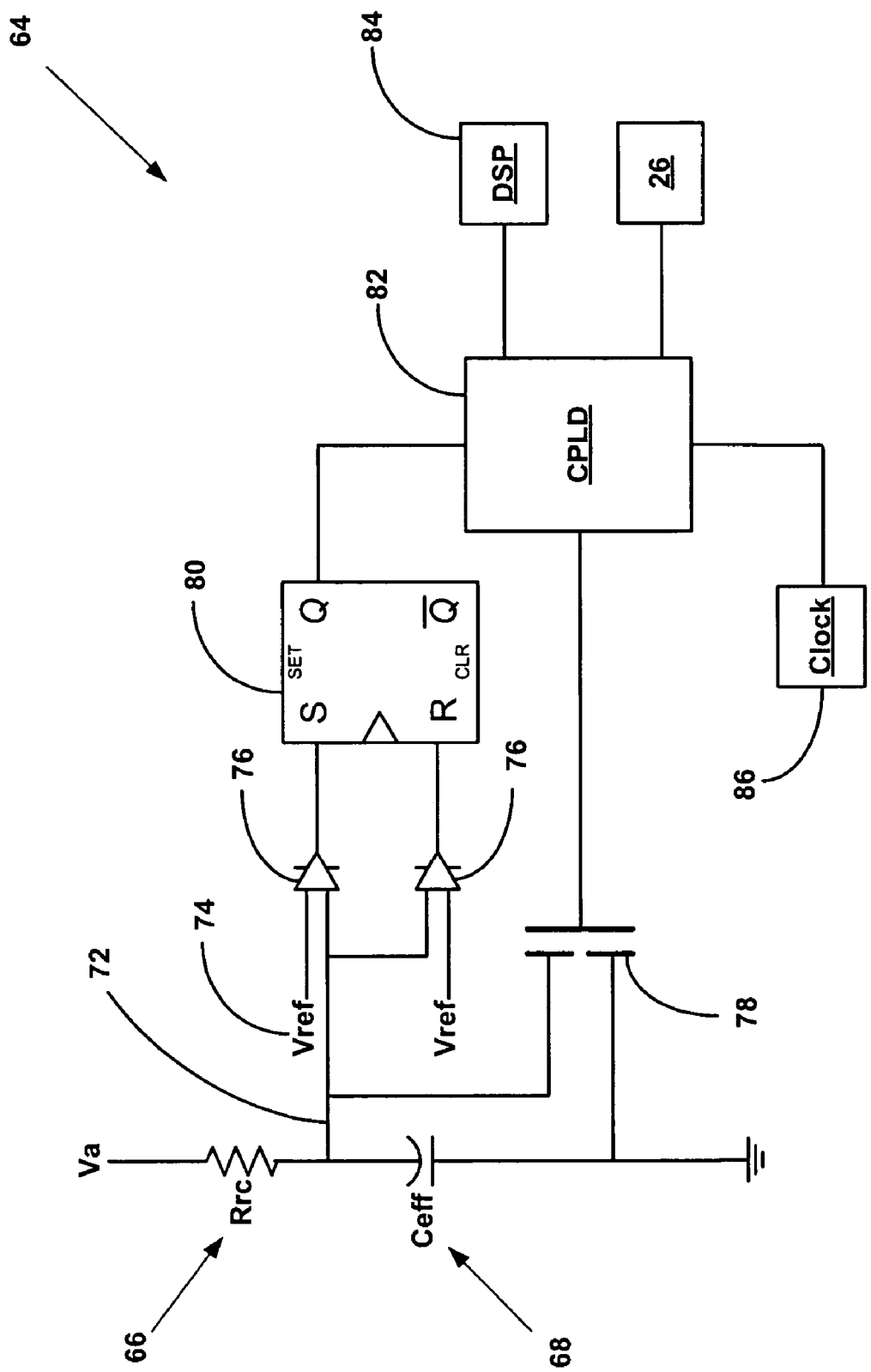
FIG. 3 is a schematic representation of the liquid level sensor of the present invention.

The present invention achieves these improvements using a time-based voltage measuring circuit like that illustrated in FIG. 3 wherein is shown a block diagram of the functional theory of operation for the liquid level sensor 64. The basic premise of this circuit is based on the charging of unknown external capacitance Ceff 68 of needle 56. As shown in FIG. 3, the liquid level sensor 64 of the present invention consists of known fixed resistor Rrc 66 and unknown external capacitance Ceff 68 of needle 56, the measured voltage 72 of which is applied to a set of comparators 76, for example operational amplifiers 76. A reference voltage Vref 74 is applied to comparators 76. As shown, the capacitance Ceff 68 of needle 56 will exponentially charge from 0 volts at time $t_0$ to eventually equal the applied voltage Va. The amount of time required to reach the Vref 74 voltage is dependent on the RC time constant of liquid level sensor 64 as given in Formula 1 below.

$$Vref = Va(1 - e^{-time/RC})$$  Formula 1

In operation and starting at an initial time $t_0$, the voltage of the RC network portion of liquid level sensor 64 is set to 0 volts using a Field Effect Transistor FET latch 78 to discharge the RC network capacitance to ground. Since the RC network voltage 72 is less than Vref 74, the set of comparators 76 causes the output of a flip-flop 80 to send a high state signal to a Complex Programmable Logic Device CPLD 82. CPLD 82 is programmed to then turn FET 78 off causing two things to happen:

1. The voltage to the two comparators 76 will begin to rise exponentially.
2. A Counter 86, typically comprising a 100 MHz clock and a latch, is enabled to count and begins counting.

When the voltage of the RC network applied to the two comparators 76 is slightly greater than Vref 74, the two comparators 76 set flip-flop 80 to the low state of CPLD 82. The low transition causes programming within CPLD 82 to:

1. Latch the time count, thus determining the time to reach Vref 74;
2. Send an interrupt to a Digital Signal Processor DSP 84 to read the count; and,
3. Turn on the discharge signal to FET 78 for a fixed time to discharge the voltage of the RC network.

When the count data has been read by DSP 84, a "Read Done" signal is sent to CPLD 82 which causes FET latch 78 to be released, grounding the capacitance Ceff 68 of needle 56, and interrupting the count signal from counter 86 going to DSP 84. This charging-discharging-recharging process is continuously repeated with DSP 84 reading each successive time interval required for capacitance Ceff 68 to charge to Vref 74.

Figure 4:
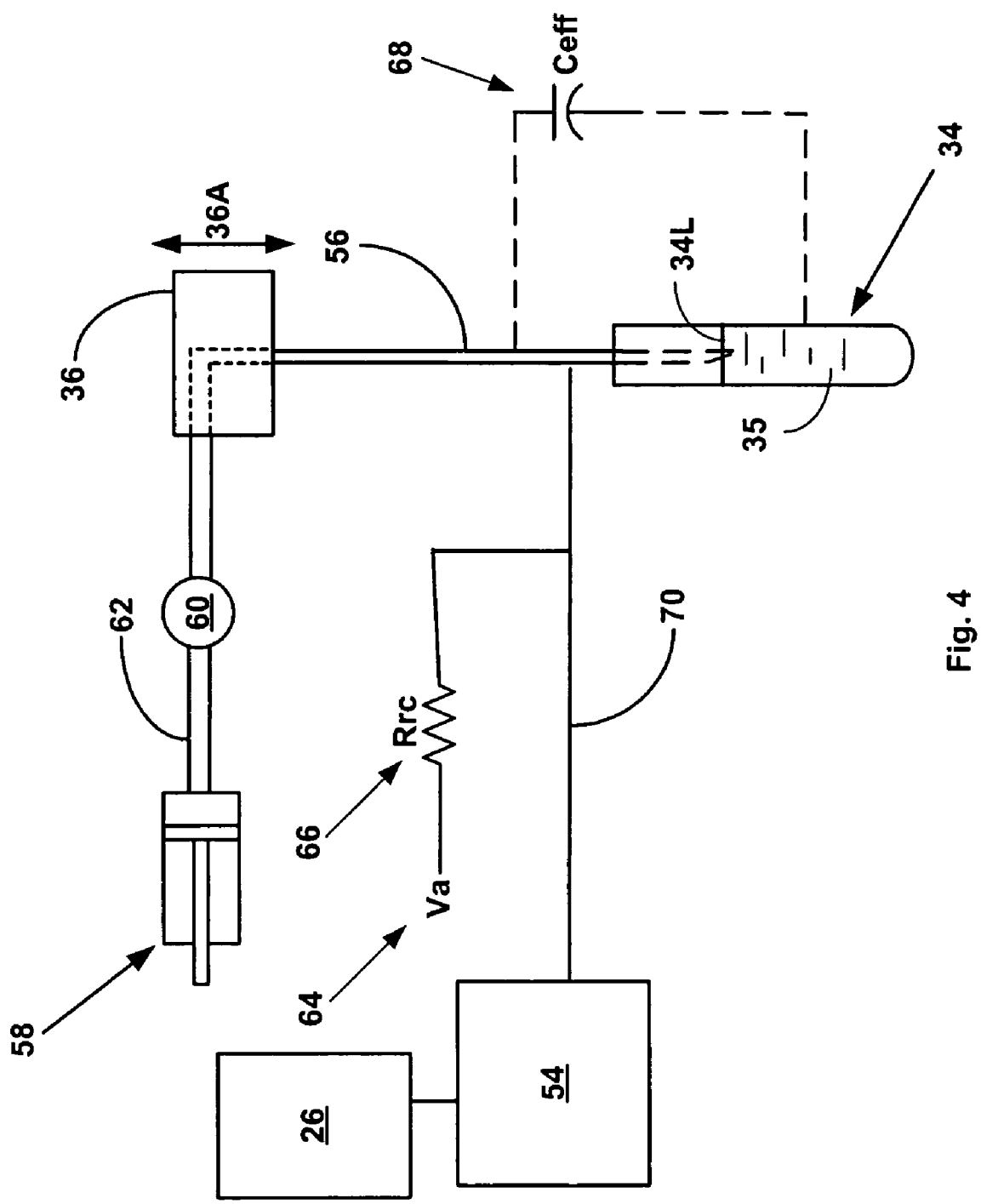
FIG. 4 is a block diagram of the liquid sensor of the present invention with a probe submerged in liquid; and, FIG. 5 is a timing diagram for the liquid level sensor of the present invention.

From the above description, it is clear that as long as needle 56 is above the uppermost level 34L of a sample liquid 35 contained in tube 34, illustrated in FIG. 2, the capacitance Ceff 68 of needle 56 will remain constant and in accord with Formula 1, DSP 84 will continue to read a number of constant successive periods of time, counts by counter 86, required for capacitance Ceff 68 to charge to Vref 74. However, as illustrated in FIG. 4, when needle 56 is lowered by aspiration probe 36 and penetrates the uppermost level 34L of a sample liquid 35, the capacitance Ceff 68 of needle 56 will abruptly step-wise increase to a higher value, and in accord with Formula 1, longer successive periods of time will be required for the higher capacitance Ceff 68 to charge to Vref 74 so that DSP 84 will read a number of longer constant successive periods of time, relatively higher counts by counter 86, in discharge-charge cycles as long as needle 56 is below the uppermost level 34L of a sample liquid 35.

This change to a relatively higher count value when needle 56 penetrates the uppermost level 34L of a sample liquid 35 is shown in FIG. 5 in which C1count represents the periods of time in discharge-charge cycles of the capacitance Ceff 68 of needle 56 while needle 56 is above the uppermost level 34L of a sample liquid 35. Correspondingly, C2count represents the periods of time in discharge-charge cycles of the capacitance Ceff 68 of needle 56 while needle 56 is below the uppermost level 34L of a sample liquid 35. The sensitivity of liquid level sensor 64 is established by empirically predetermining the number of counts that C2count is higher than C1count when needle 56 penetrates the uppermost level 34L of a sample liquid 35. In subsequent operation of liquid level sensor 64, DSP 84 is employed to make this comparison between C2count as measured relative to C1count. For purposes of clarity in illustration only, the scale at which FIG. 5 is drawn indicates that C2count is about 33% higher than C1 count whereas in practice the increase will be much smaller, in the order of 2–5% for a highly sensitive liquid level sensor 64.

A key factor in the present invention is further using DSP 84 to calculate a running average of counts made by counter 86 over a number of discharge-charge cycles in order to verify that any change in counts between discharge-charge cycles is a persistent change and is therefore not caused by false signals arising from factors such as foam, bubbles, electrical disturbances and the like but is the result of actual penetration of liquid level 34L by needle 56. The number of discharge-charge cycles to be averaged may be varied depending upon the nature of the aspiration process but generally a number in the range of 3 to 7 cycles has been found to be sufficient for the aspiration of patient liquid samples. Verification that the higher counts between discharge-charge cycles is persistent, and is not a false trigger, can be accomplished by simply interrogating DSP 84 to confirm that the higher count level has been maintained. It is this verification that can be established by predetermining the sensitivity of the liquid level sensor 64 that is an improvement over prior art sensors.

As an example, while needle 56 is passing in open air the effective capacitance of needle 56 may cause counter 86 to read in the range of 10,000 to 10,020 counts. When needle 56 touches liquid level 34L, the count may abruptly change to 10,200 counts because of the increase in effective capacitance of needle 56. If the sensitivity of the circuitry of liquid level sensor 64 was selected to be 180 counts, then penetration of liquid level 34L by needle 56 would be detected.

It should be readily appreciated by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. For example, computer 26 may readily be adapted to receiving any change in the averaged charging time from signal processor 84 and be programmed to maintain needle 56 below the uppermost level 34L of a liquid in response to any change in the averaged charging time.

Accordingly, while the present invention has been described herein in detail in relation to specific embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. A capacitive liquid level sensor, the sensor comprising:
   an aspiration probe needle adapted to be vertically translatable relative to the uppermost level of a liquid in a container and having an effective capacitance therebetween;
   a source of a fixed voltage applied to said probe through a fixed resistor forming a RC network;
   a source of a reference voltage;
   a comparator circuit adapted to compare the RC network and reference voltages;
   means for repeatably discharging and charging the RC network;
   a counter for counting the time required for repeatably discharging and charging the RC network;
   a signal processor for averaging the charging time over a number of successive discharging and charging of the RC network,
   said signal processor further adapted to identify any change in the averaged charging time that exceeds a pre-determined value as a consequence of the needle penetrating the uppermost level of the liquid.

2. The sensor of claim 1 further comprising means for confirming that such a change in the averaged charging time is stable over a pre-determined time period.

3. The sensor of claim 2 further comprising means for rejecting as invalid any changes in the averaged charging time that are not stable over said pre-determined time period.

4. The sensor of claim 1 further comprising interrogating means for subsequently verifying that the change in the averaged charging time exceeds a pre-determined value.

5. The sensor of claim 1 wherein the predetermined value is in the range of 2–5% of the averaged charging time.

6. The sensor of claim 1 wherein averaging the charging time over a number of successive discharging and charging of the RC network comprises averaging the charging time over 3 to 7 successive discharging and charging of the RC network.

7. The sensor of claim 1 wherein the comparator circuit comprises a pair of operational amplifiers.

8. An analyzer comprising the sensor of claim 2, the analyzer having a computer receiving any change in the averaged charging time from the signal processor, the computer programmed to maintain the position of the needle below the uppermost level of a liquid in response to any said change in the averaged charging time.

* * * * *